(12) United States Patent
Jensen et al.

(10) Patent No.: US 7,829,017 B2
(45) Date of Patent: Nov. 9, 2010

(54) STERILIZATION SYSTEM FOR STERILIZING AND/OR NEUTRALIZING THE ACTIVITY OF MICROORGANISMS IN LIQUIDS AND GASES, AND STERILIZATION AND/OR NEUTRALIZATION PROCESS

(75) Inventors: Jens Dahl Jensen, Berlin (DE); Hendrik Rönsch, Berlin (DE)

(73) Assignee: Siemens Aktiengesellschaft, Munich (DE)

( * ) Notice: Subject to any disclaimer, the term of this patent is extended or adjusted under 35 U.S.C. 154(b) by 381 days.

(21) Appl. No.: 11/997,375

(22) PCT Filed: Jul. 20, 2006

(86) PCT No.: PCT/EP2006/064448
§ 371 (c)(1),
(2), (4) Date: Jan. 30, 2008

(87) PCT Pub. No.: WO2007/017354
PCT Pub. Date: Feb. 15, 2007

(65) Prior Publication Data
US 2008/0226494 A1    Sep. 18, 2008

(30) Foreign Application Priority Data
Aug. 5, 2005    (DE) ............... 10 2005 037 849

(51) Int. Cl.
*A61L 2/23* (2006.01)
*A61L 2/03* (2006.01)
*A61L 2/232* (2006.01)
*A61L 2/238* (2006.01)

(52) U.S. Cl. .................. 422/28; 422/186.01
(58) Field of Classification Search .......... 422/28, 422/186.01; 430/111.31
See application file for complete search history.

(56) References Cited

U.S. PATENT DOCUMENTS

| | | | |
|---|---|---|---|
| 3,970,530 A | 7/1976 | Maslowski et al. | 426/237 |
| 5,180,557 A * | 1/1993 | Priestley, Jr. | 422/130 |
| 5,411,832 A * | 5/1995 | Yoerger | 430/111.32 |
| 5,843,186 A * | 12/1998 | Christ | 623/6.56 |
| 6,294,304 B1* | 9/2001 | Sukovich et al. | 430/111.31 |
| 6,393,975 B2 | 5/2002 | Morshuis et al. | 99/451 |
| 2003/1390475 | 10/2003 | Everett | 428/403 |
| 2005/0048570 A1* | 3/2005 | Weber et al. | 435/7.1 |

FOREIGN PATENT DOCUMENTS

| | | |
|---|---|---|
| DE | 19800294 A1 | 7/1999 |
| DE | 60100765 T2 | 7/2004 |
| FR | 2240020 A | 3/1975 |
| GB | 202143 A | 8/1923 |
| WO | 9827896 A | 7/1998 |
| WO | 2004045577 A | 6/2004 |

* cited by examiner

*Primary Examiner*—Sean E Conley
*Assistant Examiner*—Christopher K VanDeusen
(74) *Attorney, Agent, or Firm*—King & Spalding L.L.P.

(57) ABSTRACT

In a sterilisation system for sterilising and/or neutralising the activity of micro-organisms in liquids and gasses, and in a sterilisation and/or neutralisation process, sterilisation is carried out by exposing the micro-organisms to a potential difference ranging from 200 to 1000 mV.

4 Claims, 1 Drawing Sheet

STERILIZATION SYSTEM FOR STERILIZING AND/OR NEUTRALIZING THE ACTIVITY OF MICROORGANISMS IN LIQUIDS AND GASES, AND STERILIZATION AND/OR NEUTRALIZATION PROCESS

CROSS-REFERENCE TO RELATED APPLICATIONS

This application is a U.S. national stage application of International Application No. PCT/EP2006/064448 filed Jul. 20, 2006, which designates the United States of America, and claims priority to German application number 10 2005 037 849.8 filed Aug. 5, 2005, the contents of which are hereby incorporated by reference in their entirety.

TECHNICAL FIELD

The field of the invention concerns the sterilization/neutralization of the activity of microorganisms in liquids and gases. This is usually carried out by means of techniques such as

- mixing the liquid/gas with chemical agents such as for instance chlorine, ozone (in particular in the case of drinking water) or metal ions such as copper or silver compounds
- radioactive or UV radiation
- brief heating (pasteurization).

These techniques have the disadvantage, however, that the liquid or gas that is to be sterilized is often also influenced at the same time, for instance by the chemical sterilizing agents remaining in the liquid. It is also not possible to rule out an influence taking place when radiation is used for heating or mixing, for instance in the case of foodstuffs.

SUMMARY

There exists a need for a sterilization system that is capable of carrying out sterilization and/or neutralization of the activity of microorganisms in liquids and gases largely without having any influence.

According to an embodiment, a sterilization system for the sterilization and/or neutralization of the activity of microorganisms in liquids and/or gases, may comprise particles in which at least one oxidizing agent and at least one reducing agent are arranged in such a way that a potential difference ranging from $\geq 200$ to $\leq 1000$ mV is achieved. According to another embodiment, a process for sterilizing liquids or gases, may comprise the steps of arranging in a reactor particles with at least one oxidizing agent and at least one reducing agent in such a way that a potential difference ranging from $\geq 200$ to $\leq 1000$ mV is achieved; fixing the sterilization system by applying a magnetic field; and passing the liquid or gas that is to be sterilized through the reactor. According to a further embodiment, the particles may have a particle diameter ranging from $\geq 20$ nm to $\leq 10$ μm. According to a further embodiment, the oxidizing agent and/or the reducing agent may have an exchange current density ranging from $\geq 10^{-3}$ A/cm$^2$ to $\leq 100$ A/cm$^2$. According to a further embodiment, the oxidizing agent may be selected from the group comprising Ag, Au, Cu, Co, Ni or mixtures thereof. According to a further embodiment, the reducing agent may be selected from the group comprising Pd, Pt, Rh, Ir or mixtures thereof. According to a further embodiment, the particles additionally may contain at least one ferromagnetic component. According to a further embodiment, the ferromagnetic component may be provided in the particles as a core which is surrounded by the oxidizing agent and/or the reducing agent.

DETAILED DESCRIPTION

Figure 1:
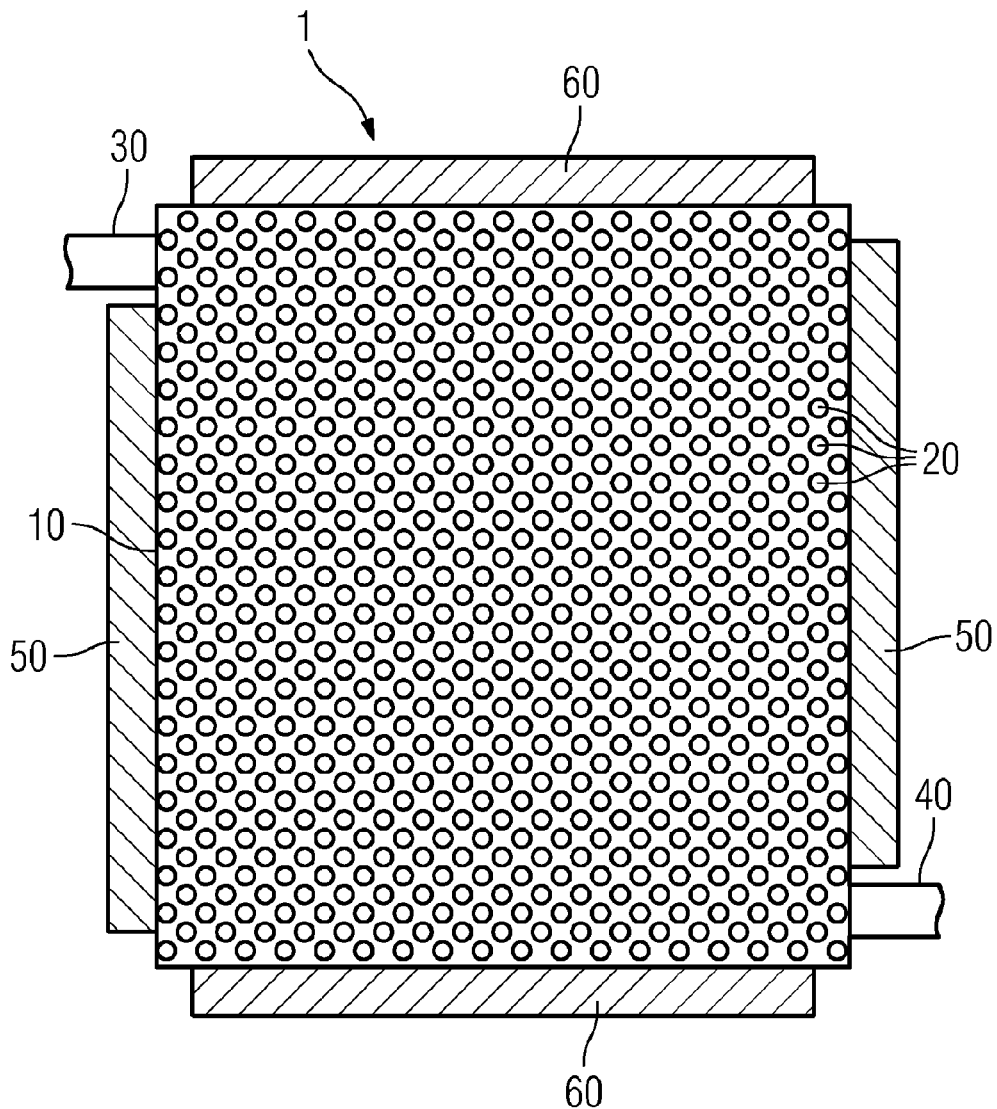
FIG. 1 shows a sterilization system in the form of particles, arranged in a flow reactor according to a first embodiment, in a—very schematic—sectional view.

According to an embodiment, a sterilization system for the sterilization and/or neutralization of the activity of microorganisms in liquids and/or gases is provided, characterized in that the sterilization is brought about by the microorganisms being exposed to a potential difference ranging from $\geq 200$ to $\leq 1000$ mV.

Sterilization is understood as meaning in particular disinfection and/or sterilization. Disinfection means in particular a reduction of germs by a factor of at least $10^{-5}$, i.e., out of originally 100,000 germs capable of reproduction (known as colony forming units—CFUs), no more than a single germ survives. It is preferred that, according to various embodiments, sterilization is understood as meaning neutralization of the liquid and/or the gas, the term "neutralization" being understood in particular in the sense of a reduction of germ-forming units by a factor of at most $10^{-6}$, i.e., out of a million germs, at most one survives.

According to various embodiments, microorganisms are understood as meaning in particular bacteria, fungi, animal and plant protozoa and metazoa, but also DNA (and fragments), RNA (and fragments), plasmids and similar artefacts as well as viruses and spores.

According to various embodiments, potential difference is understood as meaning in particular the difference between electrochemically measurable corrosion potentials in every type of electrolyte. According to various embodiments, corrosion potentials are measured in particular as standard values with respect to a standard reference electrode, for example a hydrogen electrode, whereby the individual metallic elements can be classified in an ordered voltage series. Preferred here in particular is the standard voltage series, measured in water at 25 degrees Celsius with respect to a standard hydrogen reference electrode.

A sterilization system according to various embodiments is distinguished, inter alia, by one or more of the following advantages:

- the fact that scarcely any materials are consumed means that it is very sparing in its use of resources and is also usually low in maintenance;
- in most applications, the fluid to be sterilized is not influenced, or scarcely at all, so that the sterilization system according various embodiments is also suitable for sterilizing foodstuffs;
- the fact that the sterilization is performed by using a potential difference means that the sterilizing operation is also very efficient and time-saving in comparison with most other conventional processes.

With preference, the microorganisms are exposed to a potential difference ranging from $\geq 300$ to $\leq 900$ mV, with even greater preference $\geq 400$ to $\leq 800$ mV and with greatest preference $\geq 500$ to $\leq 700$ mV.

According to an embodiment, the system comprises particles in which at least one oxidizing agent and at least one reducing agent are arranged in such a way that a potential difference ranging from ≧200 to ≦1000 mV is achieved. This makes it possible to sterilize a large amount of liquid with a high throughput. With preference, the system may comprise particles in which at least one oxidizing agent and at least one reducing agent are arranged in such a way that a potential difference ranging from ≧300 to ≦900 mV, with even greater preference ≧400 to ≦800 mV and with greatest preference ≧500 to ≦700 mV is achieved.

It should be pointed out that, as far as electrochemical nomenclature is concerned, the oxidizing agent acts or can be referred to as the cathode and the reducing agent acts or can be referred to as the anode.

According to another embodiment, the particles may have a particle diameter ranging from ≧20 nm to ≦10 μm. Particles of this size are particularly suitable for sterilization, since on the one hand the surface area/volume ratio is particularly favorable, and on the other hand the particles are not so small that they can only be poorly handled. With preference, the particles may have a particle diameter ranging from ≧50 nm to ≦1 μm, with greater preference ≧100 nm to ≦800 nm, and with greatest preference ranging from ≦200 nm to ≦500 nm.

According to another embodiment, the oxidizing agent and/or the reducing agent has an exchange current density ranging from $\geq 10^{-3}$ A/cm$^2$ to $\leq 100$ A/cm$^2$. Such an exchange current density has the effect of maintaining a consistently good potential difference even when the particles are in use for quite a long time. With preference, the oxidizing agent and/or the reducing agent may have an exchange current density ranging from $\geq 10^{-2}$ A/cm$^2$ to $\leq 20$ A/cm$^2$, with greater preference $\geq 0.1$ A/cm$^2$ to $\leq 15$ A/cm$^2$, and with greatest preference $\geq 0.15$ A/cm$^2$ to $\leq 10$ A/cm$^2$.

According to another embodiment, the oxidizing agent may be selected from the group comprising Ag, Au, Cu, Co, Ni or mixtures thereof. These oxidizing agents have been found in practice to be the best suited oxidizing agents.

According to another embodiment, the reducing agent may be selected from the group comprising Pd, Pt, Rh, Ir or mixtures thereof. These reducing agents have been found in practice to be the best suited reducing agents.

According to another embodiment, the particles additionally contain at least one ferromagnetic component. This makes it possible to fix the particles by applying a suitable magnetic field, for example in a flow reactor.

Magnetic nanoparticles and a process for producing these particles are presented for example in US 2003 0190475; however, these nanoparticles are not suitable for a sterilization system according to various embodiments.

According to another embodiment, the ferromagnetic component may be provided in the particles as a core which is surrounded by the oxidizing agent and/or the reducing agent. This has been found to be a particularly favorable arrangement.

According to another embodiment, the ferromagnetic component is selected from the group comprising Fe, Ni, Co or mixtures thereof. These materials have been found in practice to be particularly advantageous.

According to yet another embodiment, a process for sterilizing liquids or gases, may comprise the steps of:
 providing a sterilization system as described above in a reactor
 fixing the sterilization system by applying a magnetic field
 passing the liquid or gas that is to be sterilized through the reactor.

The components to be used according to an embodiment that are mentioned above and those that are claimed and described in the exemplary embodiments are not subject to any special exceptional conditions in terms of their size, shape, material selection and technical conception, and so the selection criteria known in the field of application can be applied unrestrictedly.

Further details, features and advantages of the subject matter of the invention emerge from the following description of the associated drawings, in which a number of exemplary embodiments of the sterilization system according to the invention are represented—by way of example.

FIG. 1 shows a sterilization system 1 in the form of particles 20, arranged in a flow reactor 10 according to a first embodiment in a schematic sectional view. The particles are fixed in the flow reactor in a desired way by an external magnetic field. For this purpose, in this embodiment external magnets 50, 60 are provided on the reactor, it being possible for them to be formed either as permanent magnets or as magnetizable electric components such as coils etc.

The fluid to be sterilized enters the reactor at the inlet 30 and leaves it, once it has passed the particles 20, through the outlet 40.

Figure 2:
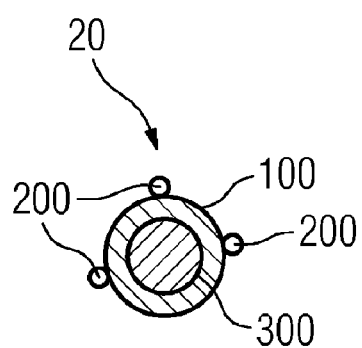
FIG. 2 shows a particle from FIG. 1 in a—very schematic—sectional view.

FIG. 2 shows a particle from FIG. 1 in a—very schematic—sectional view. This particle comprises a core 300, which is made of a ferromagnetic material. With preference, the core is of iron. Around the core is a reducing agent 100, which in this embodiment comprises silver. However, all other previously mentioned reducing agents are also conceivable. Apart from the reducing agent 100, a number of local elements 200 are also arranged, comprising the oxidizing agent. In this embodiment, the oxidizing agent is palladium, but here too all other previously mentioned oxidizing agents are also conceivable.

As they pass the particles 20, the microorganisms in the fluid are exposed to the potential difference between the reducing agent 100 and the oxidizing agent 200 and in this way the fluid is sterilized.

What is claimed is:

1. A process for sterilizing liquids or gases, comprising the steps of:
 providing in a reactor a plurality of particles, each of the plurality of particles comprising a ferromagnetic core material, a reducing agent material surrounding the ferromagnetic core material and at least one oxidizing agent material in electrochemical communication with the reducing agent material, wherein a potential difference between the reducing agent material and the at least one oxidizing agent material ranges from ≧200 to ≦1000 mV, and wherein the oxidizing agent is any one or an alloy selected from the group consisting of Ag, Au, Cu, Co, and Ni;
 arranging the plurality of particles in the reactor by applying a magnetic field thereto; and
 passing the liquid or gas to be sterilized through the reactor and around the plurality of particles arranged therein.

2. The process according to claim 1, wherein each of the plurality of particles has a particle diameter ranging from ≧20 nm to ≦10 μm.

3. The process according to claim 1, wherein the plurality of particles has an exchange current density ranging from $\geq 10^{-3}$ A/cm$^2$ to $\leq 100$ A/cm$^2$.

4. The process according to claim 1, wherein the reducing agent is any one or an alloy selected from the group consisting of Pd, Pt, Rh, and Ir.

* * * * *